United States Patent [19]

Herman

[11] 4,292,211

[45] Sep. 29, 1981

[54] FRAGRANCE DISPERSANT COMPOSITION

[75] Inventor: Justin Herman, Norwalk, Conn.

[73] Assignee: Shaw Mudge & Company, Stamford, Conn.

[21] Appl. No.: 174,003

[22] Filed: Jul. 31, 1980

[51] Int. Cl.[3] .......................... A61K 7/46; C11B 9/00; C11D 3/50; C11D 7/32

[52] U.S. Cl. .................................... 252/529; 252/139; 252/153; 252/173; 252/174.11; 252/522 R; 252/523; 252/526; 252/531; 252/532; 252/545; 252/548; 252/DIG. 14

[58] Field of Search ................... 252/522 R, 139, 153, 252/173, 174.11, 526, 529, 531, 532, 545, 548, 550, 551, DIG. 13, DIG. 14; 424/70, 320

[56] References Cited

U.S. PATENT DOCUMENTS

| | | | |
|---|---|---|---|
| 3,095,381 | 6/1963 | Tinnon et al. | 252/161 |
| 3,561,262 | 2/1971 | Borucki et al. | 73/104 |
| 3,876,551 | 4/1975 | Laufer | 252/98 |
| 4,054,541 | 10/1977 | Mausner et al. | 252/532 |
| 4,061,150 | 12/1977 | Dasher | 424/70 |
| 4,077,911 | 3/1978 | Okumura et al. | 252/550 |
| 4,170,655 | 10/1979 | Zeidler | 424/320 |

OTHER PUBLICATIONS

Ruth Winter, A Consumer's Dictionary of Cosmetic Ingredients, 1974, p. 16.

Arthur and Elizabeth Rose, The Condensed Chemical Dictionary, 1961, pp. 12, 452, 1045.

*Primary Examiner*—Dennis L. Albrecht

*Attorney, Agent, or Firm*—St. Onge, Steward, Johnston, Reens & Noe

[57] ABSTRACT

A fragrance dispersant composition for dispersing fragrance oil in an aqueous hard surface cleanser comprising a mixture of N(2-hydroxyethyl)acetamide, anionic surfactant capable of mixing with said N(2-hydroxyethyl)acetamide to form a homogeneous solution, and fragrance oil. The fragrance dispersant composition may be mixed with water and one or more detergents to formulate an aqueous hard surface cleanser.

17 Claims, No Drawings

FRAGRANCE DISPERSANT COMPOSITION

BACKGROUND OF THE INVENTION

1. Field of the Invention

This invention relates to a fragrance dispersant composition for dispersing fragrance oil in an aqueous hard surface cleanser. More particularly, the present invention relates to a fragrance dispersant composition that will enable the use of many fragrance oil types in aqueous hard surface cleansers.

2. Description of the Prior Art

Conventional aqueous hard surface cleansers are known to contain one of two fragrance types, pine or lemon. It has been a common practice in cleansers to solubilize pine or lemon fragrances by using either ethoxylated polysorbate esters or ethoxylated phenol based alcohols with a ratio of solubilizer to fragrance oil being in the order of about 2 to 1 parts by weight to about 5 to 1 parts by weight. Heretofore, fragrances other than pine and lemon have been very difficult to use with hard surface cleansers since they do not disperse readily in such compositions.

Some prior attempts to incorporate various fragrance compositions into aqueous hard surface cleansers required heating, resulting in substantial losses of the volatile fragrance.

It is a principal object of the present invention to provide a fragrance dispersant composition for dispersing various types of fragrance oil in aqueous hard surface cleansers. More specifically, it is an object of the present invention to provide a fragrance dispersant composition for dispersing fragrance oil types such as complex floral bouquets, herbals, spice notes and other complex fragrance types in addition to pine and lemon fragrance types in an aqueous hard surface cleanser.

SUMMARY OF THE INVENTION

A fragrance dispersant composition in accordance with the present invention comprises a mixture of N(2-hydroxyethyl)acetamide, one or more anionic surfactants capable of mixing with said N(2-hydroxyethyl)acetamide to form a homogeneous solution, and fragrance oil. The fragrance dispersant composition may be used for dispersing fragrance oil in an aqueous hard surface cleanser. By use of a mixture of N(2-hydroxyethyl)acetamide and one or more anionic surfactants, various types of fragrance oils are readily and uniformly solubilized in an aqueous hard surface cleanser. Such fragrance oil types include complex floral bouquets, herbals, spice notes and other complex combinations as well as lemon and pine fragrance oil types.

An aqueous hard surface cleanser is formulated by mixing the fragrance dispersant composition with water and one or more detergents. The type of fragrance oil in the aqueous cleanser is selected with a view to the environment where the aqueous cleanser is to be used. For example, an aqueous cleanser intended for use in a kitchen may include a floral bouquet fragrance oil whereas an aqueous cleanser intended for use in a bathroom may include a herbal fragrance oil.

DETAILED DESCRIPTION OF THE INVENTION

A fragrance dispersant composition for formulating aqueous hard surface cleansers in accordance with the present invention comprises a mixture of N(2-hydroxyethyl)acetamide, one or more anionic surfactants capable of mixing with said N(2-hydroxyethyl)acetamide to form a homogeneous solution, and fragrance oil. The fragrance dispersant composition in accordance with the preferred embodiment of the invention includes from about 50 to about 80 percent by weight N(2-hydroxyethyl)acetamide, preferably 60 to 80 percent by weight and most preferably 65 to 75 percent. The fragrance dispersant composition also contains from about 15 to about 35 percent by weight anionic surfactant capable of mixing with said N(2-hydroxyethyl)acetamide to form a homogeneous solution, and preferably about 20 to about 30 weight percent anionic surfactant and most preferably about 25 to about 30 weight percent anionic surfactant. The fragrance dispersant composition also includes between about 1 and about 16 weight percent fragrance oil. If the weight percent of perfume oil in the fragrance dispersant composition is reduced below about 1 weight percent, it has been found that the scent of an aqueous hard surface cleanser formulated with the fragrance dispersant composition is not sufficiently strong. The proper amount of fragrance oil will depend on the type with fragrance strength and cost being important factors. If the weight percent of the fragrance oil exceeds about 10, the fragrance oil may no longer be completely soluble in the N(2-hydroxyethyl)acetamide and anionic surfactant mixture.

The anionic surfactant in the fragrance dispersion composition of the present invention is selected so that it is capable of mixing with N(2-hydroxyethyl)acetamide to form a homogeneous solution. It is preferred that an alkyl (from $C_8$ to $C_{18}$) sulfate surfactant which is capable of mixing with the N(2-hydroxyethyl)acetamide to form a homogeneous solution be used. The most preferred surfactants include sodium lauryl ether sulfate, ammonium lauryl sulfate and triethanolamine lauryl sulfate with sodium lauryl ether sulfate having a level of ethoxylation within the range of about 1 to about 32 moles of ethylene oxide per mole of sodium lauryl sulfate being most preferred.

The N(2-hydroxyethyl)acetamide for use in the fragrance dispersant composition has the following structural formula:

$$CH_3-\overset{\overset{\displaystyle O}{\|}}{C}-NH-CH_2-CH_2OH$$

N(2-hydroxyethyl)acetamide, or acetamide MEA as it is commonly known, is a known ingredient in cosmetic products and is used in shampoos and hair conditioners to add "body" to hair, that is, to increase the thickness of the individual hair fibers and thereby increase the bulk density of the hair and is also known to reduce the buildup of static electricity in hair, thus making the hair more manageable.

It has been determined that if either the N(2-hydroxyethyl)acetamide or the anionic surfactant is eliminated from the fragrance dispersant composition, the ability to solubilize various fragrances is substantially reduced or completely eliminated.

The above described fragrance dispersant composition is particularly useful for formulating aqueous hard surface cleansers. The fragrance dispersant composition containing N(2-hydroxyethyl)acetamide, anionic surfactant and fragrance oil is mixed with water and one or more detergents and solvents to form a mixture which may be used as an aqueous hard surface cleanser, i.e. a cleanser for floors, tiles, porcelain, and the like. An aqueous hard surface cleanser in accordance with the present invention comprises, in approximate weight percent range, the following:

| INGREDIENT | WEIGHT PERCENT RANGE | PREFERRED WEIGHT PERCENT RANGE |
|---|---|---|
| Water | 30 to about 95 | 65 to about 92 |
| N(2-hydroxyethyl)-acetamide | 1 to about 40 | 2 to about 15 |
| Anionic Surfactant | 0.5 to about 16 | 0.2 to about 10 |
| Fragrance Oil | 0.05 to about 6 | 0.1 to about 0.5 |
| One or more Detergents and solvents | 3 to about 15 | 15 to about 8 |

The detergents and solvents may be selected from conventional detergents which are soluble in the above described hard surface cleanser and include tetrasodium pyrophosphate, trisodium phosphate, sodium metasilicate, and 2-butoxyethanol.

A hard surface cleanser formulated in accordance with the present invention has the additional advantageous property that it imparts antistatic properties to the surface being cleaned. A surface cleaned with the aqueous hard surface cleaner in accordance with the present invention will tend to remain lint free a considerable time after use of the cleanser. The antistatic property of the hard surface cleanser is particularly useful to avoid accumulation of dust on surfaces such as countertops, floors, appliances and the like.

This invention will be further described in detail by reference to the following illustrative examples.

EXAMPLES 1-5

The following examples show formulations of fragrance dispersant compositions. The N(2-hydroxyethyl)acetamide and the sodium lauryl ether sulfate are mixed together at room temperature, about 25 degrees C. and then the fragrance oil is added.

| Ingredient by Weight Percent | Example 1 | Example 2 | Example 3 | Example 4 | Example 5 |
|---|---|---|---|---|---|
| N(2-hydroxyethyl) acetamide | 72.288 | 78.00 | 72.00 | 60.00 | 52.00 |
| sodium lauryl ether sulfate | 24.098 | 20.00 | 24.00 | 32.00 | 32.00 |
| fragrance oil | 3.614 | 2.00 | 4.00 | 8.00 | 16.00 |

-continued

| Ingredient by Weight Percent | Example 1 | Example 2 | Example 3 | Example 4 | Example 5 |
|---|---|---|---|---|---|
| Total | 100.00 | 100.00 | 100.00 | 100.00 | 100.00 |

The fragrance dispersant compositions described in Examples 1-5 all were clear mobile liquids and no separation occurred in these compositions after one to six months of standing at room temperature. All of the fragrance dispersant compositions may be used to formulate hard surface cleansers. Example 5 shows that a relatively large percentage of fragrance can be solubilized in the composition. It is noted that such a large percentage of fragrance oil would not normally be used because it is expensive and with certain fragrance oils, the scent may be too strong.

EXAMPLE 6

In this example, the fragrance dispersant composition of Example 1, above, was mixed with water and detergents as set forth below to provide an aqueous hard surface cleanser.

| Ingredient | | Weight Percent |
|---|---|---|
| Water, deionized | | 84.85 |
| 2-butoxyethanol | | 4.00 |
| tetrasodium pyrophosphate | | 0.50 |
| trisodium phosphate | | 1.80 |
| sodium metasilicate | | .50 |
| o-phenyl phenol | | .05 |
| fragrance disperant composition of Example 1: | | 8.30 |
| N(2-hydroxyethyl)acetamide | 6.00 | |
| sodium lauryl sulfate | 2.00 | |
| fragrance oil | 0.30 | |
| | | 100.00 |

The cleanser was clear after standing for over six months and had a pleasant scent and was thereafter used to clean a portion of the surface of a refrigerator. A cotton towel was held in contact with the cleaned surface and an untreated surface of the refrigerator immediately after the cleanser was used and lint from the towel accumulated on the untreated surface but not on the cleansed surface.

EXAMPLES 7-14

Examples 7-14 shown formulations of various aqueous hard surface including various types of surfactants and various types of fragrance oils.

| | Examples 7 through 14 | | | | | | | |
|---|---|---|---|---|---|---|---|---|
| | Ex. 7 | Ex. 8 | Ex. 9 | Ex. 10 | Ex. 11 | Ex. 12 | Ex. 13 | Ex. 14 |
| Water, dionized | 84.85 | 84.85 | 84.85 | 84.85 | 84.85 | 84.85 | 84.85 | 84.85 |
| 2-butoxyethanol | 4.00 | 4.00 | 4.00 | 4.00 | 4.00 | 4.00 | 4.00 | 4.00 |
| tetra sodium pyrophosphate | .50 | .50 | .50 | .50 | .50 | .50 | .50 | .50 |
| trisodium phosphate | 1.80 | 1.80 | 1.80 | 1.80 | 1.80 | 1.80 | 1.80 | 1.80 |
| sodium metasilicate | .50 | .50 | .50 | .50 | .50 | .50 | .50 | .50 |
| O-phenyl phenol | .05 | .05 | .05 | .05 | .05 | .05 | .05 | .05 |
| N(2-hydroxyethyl) acetamide | 6.00 | 6.00 | 6.00 | 6.00 | 6.00 | 6.00 | 6.00 | 6.00 |
| surfactant | 2.00 | 2.00 | 2.00 | 2.00 | 2.00 | 2.00 | 2.00 | 2.00 |
| | Ammonium lauryl sulfate | Ammonium lauryl sulfate | Ammonium lauryl sulfate | Ammonium lauryl sulfate | Triethanol amine lauryl sulfate | Triethanol amine lauryl sulfate | Triethanol amine lauryl sulfate | Triethanol amine lauryl sulfate |
| Fragrance oil | .30 | .30 | .30 | .30 | .30 | .30 | .30 | .30 |
| | Rose | Floral-1 | Floral-2 | Herbal | Rose | Floral-1 | Floral-2 | Herbal |
| Aqueous hard sur- | Clear | Clear | Clear | Clear | Clear | Clear | Clear | Clear |

-continued

| | Examples 7 through 14 | | | | | | | |
|---|---|---|---|---|---|---|---|---|
| | Ex. 7 | Ex. 8 | Ex. 9 | Ex. 10 | Ex. 11 | Ex. 12 | Ex. 13 | Ex. 14 |
| face cleanser appearance after standing for 30 days | | | | | | | | |

Examples 7-14 show that various types of fragrance oils can be dispersed in aqueous cleansers. Examples 6 and 7-14 show that surfactants such as sodium lauryl ether sulfate, ammonium lauryl sulfate and triethanolamine lauryl sulfate can be used in aqueous cleansers to disperse various types of fragrance oils. The aqueous cleansers of Examples 7-14 were clear after standing for over 30 days and were used to clean a refrigerator surface. The cleaned surfaces were substantially free of lint and had a smooth feel. Further, after several cleanings there was no build-up on the refrigerator surface. The fragrance in each case retained its fidelity in the cleanser and when applied.

Although the present invention has been described with reference to particular embodiments and examples, it will be apparent to those skilled in the art that variations and modifications of this invention can be made and that equivalents can be substituted therefor without departing from the principles and spirit of the invention.

What is claimed is:

1. A fragrance dispersant composition for dispersing fragrance oil in an aqueous hard surface cleanser comprising a mixture of N(2-hydroxyethyl)acetamide comprising about 50 to about 80 weight percent of the fragrance dispersant composition, about 15% or more of an anionic surfactant capable of mixing with said N(2-hydroxyethyl) acetamide to form a homogeneous solution and an effective amount of fragrance oil, said anionic surfactant being present in an amount sufficient to solubilize said fragrance oil.

2. A fragrance dispersant composition according to claim 1 wherein said N(2-hydroxyethyl)acetamide comprises about 60 to about 80 weight percent of the fragrance dispersant composition.

3. A fragrance dispersant composition according to claim 2 wherein said N(2-hydroxyethyl)acetamide comprises about 65 to about 75 weight percent of the fragrance dispersant composition.

4. A fragrance dispersant composition according to claim 1 wherein said anionic surfactant comprises about 15 to about 35 weight percent of said fragrance dispersant composition.

5. A fragrance dispersant composition according to claim 4 wherein said anionic surfactant comprises about 20 to about 30 weight percent of said fragrance dispersant composition.

6. A fragrance dispersant composition according to claim 5 wherein said anionic surfactant comprises about 25 to about 30 weight percent of said fragrance dispersant composition.

7. A fragrance dispersant composition according to claim 1 wherein said fragrance oil comprises less than about 16 weight percent of the fragrance dispersant composition.

8. A fragrance dispersant composition according to claim 7 wherein said fragrance oil comprises about 1 to about 16 weight percent of said fragrance dispersant composition.

9. A fragrance dispersant composition according to claim 1 wherein said surfactant comprises an alkyl sulfate capable of mixing with said N(2-hydroxyethyl) acetamide to form a homogeneous solution.

10. A fragrance dispersant composition according to claim 9 wherein said surfactant is selected from the group consisting of ammonium lauryl sulfate, triethanol amine lauryl sulfate and sodium lauryl ether sulfate.

11. A fragrance dispersant composition according to claim 10 wherein the surfactant is sodium lauryl ether sulfate and said sodium lauryl ether sulfate has a level of ethoxylation within the range of about 1 to about 32 moles of ethylene oxide per mole of sodium lauryl sulfate.

12. An aqueous hard surface cleanser comprising about 1 to about 40 weight percent N(2-hydroxyethyl) acetamide, about 0.5 to about 16 weight percent of one or more anionic surfactants capable of mixing with said N(2-hydroxyethyl)acetamide to form a homogeneous solution, an effective amount of fragrance oil, water, and one or more additional cleaning components suitable for use in such a cleanser.

13. A cleanser according to claim 12 wherein water comprises about 65 to about 92 weight percent of said cleanser.

14. A cleanser according to claim 13 wherein detergent comprises about 3 to about 15 weight percent of said cleanser.

15. A cleanser according to claim 14 wherein said cleanser also contains a solvent, said detergent and solvent being selected from compounds taken from the group consisting of trisodium phosphate, tetrasodium pyrophosphate, sodium metasilicate and 2-butoxyethanol.

16. A cleanser according to claim 12 wherein said anionic surfactant is an alkyl sulfate surfactant with the alkyl having a carbon chain of from $C_8$ to $C_{18}$.

17. A cleanser according to claim 16 wherein said alkyl sulfate surfactant is taken from the group consisting of sodium lauryl ether sulfate, ammonium lauryl sulfate and triethanolamine lauryl sulfate.

* * * * *